United States Patent [19]

Shih

[11] Patent Number: 5,525,229
[45] Date of Patent: Jun. 11, 1996

[54] PROCESS AND APPARATUS FOR ANAEROBIC DIGESTION

[75] Inventor: Jason C. H. Shih, Cary, N.C.

[73] Assignee: North Carolina State University, Raleigh, N.C.

[21] Appl. No.: 305,846

[22] Filed: Sep. 14, 1994

[51] Int. Cl.$^6$ ................................................. C02F 3/28
[52] U.S. Cl. .................... 210/603; 210/613; 210/615; 210/177; 210/180; 210/181; 210/320
[58] Field of Search ........................ 210/603, 605, 210/612, 613, 615, 176, 180, 181, 260, 305, 320, 177

[56] References Cited

U.S. PATENT DOCUMENTS

| | | | |
|---|---|---|---|
| 2,029,702 | 2/1936 | Buswell et al. | 210/2 |
| 2,429,589 | 10/1947 | Wiley | 195/33 |
| 3,984,286 | 10/1976 | Malick | 195/41 |
| 4,040,953 | 8/1977 | Ort | 210/6 |
| 4,100,023 | 7/1978 | McDonald | 195/27 |
| 4,213,857 | 7/1980 | Ishida et al. | 210/603 |
| 4,240,904 | 12/1980 | Dassen | 210/613 |
| 4,252,901 | 2/1981 | Fischer et al. | 435/167 |
| 4,318,993 | 3/1982 | Ghosh et al. | 210/603 |
| 4,323,367 | 4/1982 | Ghosh | 48/197 |
| 4,334,997 | 6/1982 | Peterson | 210/603 |
| 4,396,402 | 8/1983 | Ghosh | 48/197 |
| 4,401,441 | 8/1983 | Chase | 210/613 |
| 4,429,043 | 1/1984 | Paton | 210/603 |
| 4,511,370 | 4/1985 | Hunziker et al. | 48/197 |
| 4,597,872 | 7/1986 | Andersson et al. | 210/605 |
| 4,604,206 | 8/1986 | Sullivan | 210/603 |
| 4,604,361 | 8/1986 | Peters | 435/288 |
| 4,663,043 | 5/1987 | Molin et al. | 210/603 |
| 4,696,746 | 9/1987 | Ghosh et al. | 210/603 |
| 4,968,427 | 11/1990 | Glanser et al. | 210/613 |
| 5,377,917 | 1/1995 | Wiljan et al. | 210/603 |

FOREIGN PATENT DOCUMENTS

| | | | |
|---|---|---|---|
| 0078919 | 5/1983 | European Pat. Off. | 210/612 |
| 0263796 | 4/1988 | European Pat. Off. | 210/180 |
| 3243103A1 | 5/1984 | Germany . | |
| 256799 | 5/1988 | Germany | 210/603 |
| WO84/00038 | 1/1984 | WIPO . | |

OTHER PUBLICATIONS

Shih, Recent Development in Poultry Waste Digestion and Feather Utilization—A Review, Presented at the Pacific Rim Biotechnology Conference, Aug. 18–21, 1992, Taipei, Taiwan, Republic of China p. 1617 (1992).

Steinsberger et al. The Construction and Operation of A Low–Cost Poultry Waste Digester, *Biotechnology and Bioengineering* XXVI:537 (1984).

*Primary Examiner*—Peter A. Hruskoci
*Assistant Examiner*—Theodore M. Green
*Attorney, Agent, or Firm*—Bell, Seltzer, Park & Gibson

[57] ABSTRACT

A process for the anaerobic digestion of organic carbonaceous material is disclosed. The process includes the steps of (a) hydrolyzing organic carbonaceous material to produce a digester stream including hydrolysis products; (b) subjecting the digester stream to a first methanation phase operating at thermophilic conditions to produce a gaseous product including methane; and (c) subjecting the digester stream to a second methanation phase operating at mesophilic conditions to produce further gaseous product including methane, and to recover heat. An apparatus for the anaerobic digestion of organic carbonaceous material is also disclosed.

24 Claims, 1 Drawing Sheet

PROCESS AND APPARATUS FOR ANAEROBIC DIGESTION

FIELD OF THE INVENTION

The present invention relates to a process and apparatus for the anaerobic digestion of organic material, and more particularly to a three phase process and apparatus for the anaerobic digestion of organic material.

BACKGROUND OF THE INVENTION

Anaerobic digestion of organic material, such as sewage sludge, municipal waste, animal waste, industrial waste, forestry waste, agricultural waste, and other highly organic carbonaceous material, is the fermentation of such material by bacteria in the absence of oxygen. There are many benefits to anaerobic digestion of organic waste material, including stabilization of the waste, odor and solids reduction, energy production in the form of gas (primarily methane) elimination or reduction of pathogens in waste materials, production of stable, generally environmentally acceptable slurry or sludge which can be used as fertilizer, soil conditioner, or nutrient source, such as a feed supplement and the like. Anaerobic digestion is becoming increasingly important in agricultural arenas, as increasing production of intensive and large-scale production of food animals and animal products has generated an enormous waste disposal problem for the animal industry.

Typically, in conventional methanation treatments of waste, waste is treated at ambient temperatures or at mesophilic temperatures, i.e., body temperatures of about 30° to 40° C., to produce methane gas. For example, U.S. Pat. No. 4,696,746 to Ghosh et al. discloses a two-phase anaerobic digestion process with two discrete methane phase digesters operating in parallel. A source of organic feed material is delivered to an acid phase digester to degrade the organic material to volatile fatty acids or aldehydes or alcohol intermediates. Supernatant from the liquid digester contents of the acid phase digester is conveyed through a liquid conduit to a methane phase I digester. The gaseous product of the acid phase digester is conveyed through a gas conduit to a methane phase II digester. Fermentation is conducted in the methane phase I or II digester under mesophilic or thermophilic temperatures.

PCT Application No. WO 84/00038 describes a process for producing methane gas in which manure is subjected to mesophilic digestion in a first tank and afterwards to thermophilic digestion in a second tank.

U.S. Pat. No. 4,252,901 to Fisher et al. discloses a multi-stage anaerobic digestion process which includes a plurality of digestion modules, each heated by conventional means to a desired temperature.

Despite these and other processes for the anaerobic digestion of organic waste material, it would be advantageous to provide a process and apparatus for anaerobic digestion of organic material which offers simplicity in design, construction and operation and which is highly efficient in biodegradation and the production of methane gas. Further it would be advantageous to provide a process and apparatus which maximizes the energy efficiency of the digestion process. In addition, it would be advantageous to provide such a process and apparatus which provides pathogen control, and provides by-products for economic return.

SUMMARY OF THE INVENTION

The present invention provides an energy efficient process for the anaerobic digestion of organic waste material. The inventive process includes three phases for treating waste. The first phase involves hydrolyzing the organic carbonaceous material to produce a digester stream including hydrolysis products. The second phase involves subjecting the digester stream produced in the first step to a first methanation phase at thermophilic conditions. The third phase involves subjecting the digester stream to a second methanation phase at mesophilic conditions. As used herein, the phrase "digester stream" refers to the material within and passing through the digester. The digester stream may properly be characterized as "effluent" as it passes out of one chamber and as "influent" as it passes into the next. For the sake of clarity, the phase "digester stream" will be used to refer to effluent, influent, and material within a specified chamber of the digester.

In the first phase, organic carbonaceous material is hydrolyzed to produce digester stream comprising hydrolysis products. Typical hydrolysis products include short chain fatty acids, alcohols, and the like. Preferably, the step of hydrolyzing the organic carbonaceous material includes heating the material to a temperature of from about 45° C. to about 60° C. The material can be heated, for example, by adding heated water thereto, by adding steam thereto, or by other suitable methods.

The resultant digester stream is then subjected to a first methanation phase (i.e., the thermophilic methanation phase) at thermophilic conditions. The thermophilic methanation phase is operated at a temperature of from about 45° C. to about 60° C. Thermophilic methanation of the digester stream produces a gaseous product comprising methane. Preferably, the thermophilic methanation phase includes increasing the surface area available for thermophilic methanation of the digester stream, for example, by using a biofilm. The use of a biofilm in the thermophilic methanation phase provides a surface upon which the bacteria may grow. The result is an increase in the surface area available for the growth of bacteria and an enhancement of methane production.

The gaseous product is recovered, and the remaining digester stream is then subjected to a second methanation phase, at mesophilic conditions (i.e., the mesophilic methanation phase). Typically, the mesophilic methanation phase is carried out at a temperature of from about 25° C. to about 35° C. Additional gas, also comprising methane, is produced from any remaining hydrolysis products in the digester stream. Preferably, the gaseous products from both methanation phases are recovered. According to one particularly preferred embodiment, heat is recovered from the mesophilic methanation phase, and is then directed back into the process. Preferably, the recovered heat is directed into the hydrolysis phase and therefore typically less heat is added to heat the organic carbonaceous material.

The effluent stream from the second methanation phase may then be recovered for further processing, recovery, or recycling. For example, the effluent can be used in aquaculture, such as by being added to ponds as a nutrient source for fish. In addition, any sludge remaining in the digester can be dried to a solid residue or by-product and utilized as a feed supplement, fertilizer, and the like. As used herein, the term "sludge" refers to sediment which collects within the digester and is not converted to either hydrolysis products or methane gas.

The use of sequential hydrolysis, thermophilic methanation and mesophilic methanation steps offers simplicity in design, construction and operation, yet is highly efficient in biodegradation and the production of methane gas. The present invention has several advantages over conventional techniques. The second phase, thermophilic methanation, employs higher temperatures for digesting the waste than have traditionally been used. The result is a more efficient process due to the increased degradation rate. Thermophilic methanation is also known to kill pathogens in the waste.

However, the thermophilic methanation phase can result in a high heat output, which is wasted unless used otherwise. A heat exchanger in the third phase recovers heat from the digester stream which is then directed back to the hydrolyzing step, thereby increasing the energy efficiency of the process.

Also in the third phase, the mesophilic methanation phase, the remaining digester stream is treated at mesophilic temperatures. The result is an increase in the fermentation time, and a corresponding increase in methane gas production.

As another aspect, the present invention provides an apparatus for the anaerobic digestion of organic carbonaceous material. The apparatus of the present invention includes a first chamber for containing the carbonaceous material, aqueous liquid, and a source of bacteria; a second chamber in fluid communication with the first chamber for containing the digester stream, produced in the first chamber; and a third chamber in fluid communication with the second chamber for containing the digester stream produced in the second chamber. The first chamber typically has both a carbonaceous material inlet in fluid communication therewith, and an aqueous liquid inlet in fluid communication therewith. The aqueous liquid inlet is in fluid communication with an aqueous liquid source. According to one preferred embodiment, the aqueous liquid source is equipped with a heater for heating the aqueous liquid. The first chamber may be equipped with a steam injector for heating the carbonaceous material in addition to or as an alternative to providing an aqueous liquid source equipped with a heater. The second and third chambers have a source of anaerobic bacteria therein which bacteria are capable of digesting carbonaceous material. Preferably, the second and third chambers also have a bacterial growth support. According to one preferred embodiment, the apparatus also includes a heat exchanger for transferring heat from the third chamber back into the apparatus. For example, advantageously the recovered heat is directed to the aqueous liquid source and is used to heat the aqueous liquid which is added to the feed material.

BRIEF DESCRIPTION OF THE DRAWINGS

In the drawing which forms a portion of the original disclosure of the invention.

DETAILED DESCRIPTION OF THE INVENTION

Figure 1:
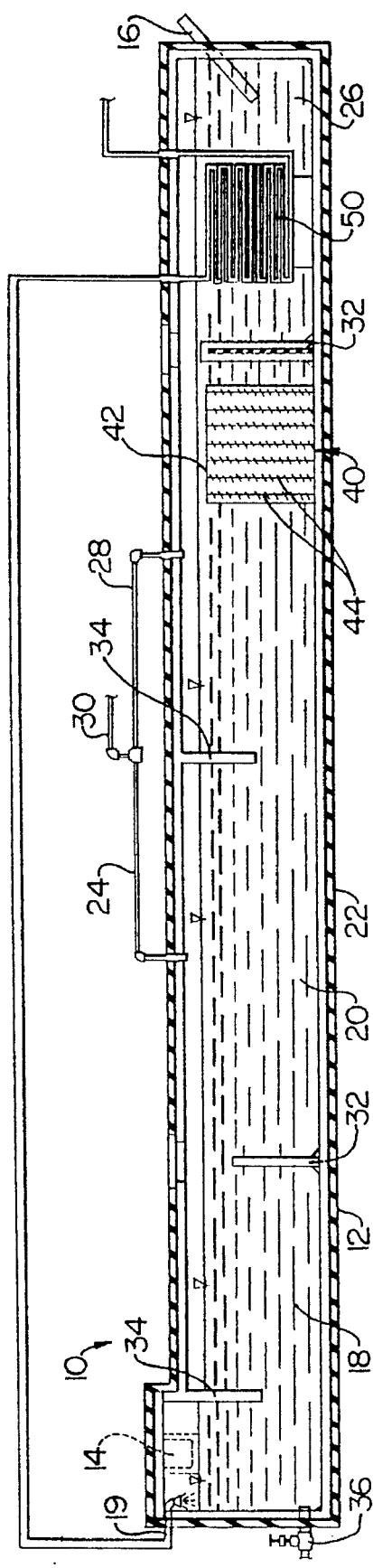
FIG. 1 schematically illustrates a side cross-sectional view of an apparatus for anaerobic digestion of organic material in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that the disclosure will be thorough and complete, and will fully convey the scope of the invention to those skilled in the art. Like numbers refer to like elements throughout. For purposes of clarity the scale has been exaggerated.

FIG. 1 is a schematic illustration of a side cross-sectional view of a digester, designated generally as 10, for anaerobic digestion of organic materials in accordance with the present invention. The digester 10 of the invention includes a generally horizontal rectangular shaped container 12 having a organic carbonaceous material inlet port 14 and an effluent removal port 16 at opposing ends of the digester 10. The digester may be located partially below ground level, or constructed above the ground.

In operation, organic carbonaceous feed material (hereinafter "carbonaceous material") is introduced into digester 10 via the carbonaceous material inlet 14, which is in fluid communication with the first chamber. The term "organic carbonaceous material" or "carbonaceous material" as used herein refers to any type of carbonaceous organic material, such as sewage sludge, municipal waste, animal waste, industrial waste, forestry waste, agricultural waste, and other highly organic carbonaceous material. The carbonaceous material can be mechanically degraded to achieve the desired particle size suitable for use in anaerobic digestion. Such mechanical processes are known in the art.

The carbonaceous material is directed from the carbonaceous material inlet 14 to a first chamber 18. The feed material can be loaded continuously or intermittently into digester 10 using techniques known in the art which utilize gravity, pumps, and the like. Also as illustrated in FIG. 1, an aqueous liquid source 19 is in fluid communication with the first chamber 18. The term "aqueous liquid" as used herein refers to liquid comprising water, wastewaters, and optionally other water soluble materials such as salts, alcohols, and the like. Preferably, the aqueous liquid employed in the present invention comprises water. The aqueous liquid dilutes the carbonaceous material to the desired solids concentration.

Typically, the carbonaceous material is heated to optimal digester temperature. Preferably, the carbonaceous material is heated to between about 45° C. to about 60° C. Heating may be accomplished by methods known to those skilled in the art. For example, in one embodiment, the aqueous liquid is heated prior to entering the first chamber 18, and warms the carbonaceous material to the desired digester operating temperature. Preferably, the aqueous liquid is heated so as to provide carbonaceous material having a temperature of about 45° C. to about 60° C. According to another embodiment, the carbonaceous material can be heated with steam, for example, by injecting steam into the first chamber 18 via a steam inlet (not shown). Providing heated aqueous liquid in the first chamber 18 is advantageous in providing controlled digestion of the carbonaceous material, as described in more detail below.

As will be appreciated by the skilled artisan, the loading rate of the carbonaceous material into the first chamber 18 will be dependent upon several factors, including retention time, the desired production of methane gas, the solids content of the organic material, etc. Preferably, the rate is about 10 kilograms to about 100 kilograms per cubic meter per day of solids, although higher or lower rates may be employed depending upon the particular carbonaceous material selected. For example, higher loading rates may be suitable for soluble, highly biodegradable carbonaceous materials such as sugars, brewing wastes, food processing wastes and the like.

Typically, the solids content of the carbonaceous material in the first chamber 18 of the digester 10 is adjusted to between about 2 to about 10 percent by weight solids, by the addition of aqueous liquid. While in the first chamber 18, the carbonaceous material undergoes hydrolysis to produce a digester stream comprising hydrolysis products. Retention time in the first chamber 18, or hydrolysis phase, can vary but should be sufficient to achieve the desired degree of hydrolysis. Typically the retention time of the carbonaceous material in the hydrolysis phase is between about one hour to about four days.

In the first chamber 18, bacteria are included which are capable of acting on the digestible carbonaceous material to hydrolyze or "depolymerize" complex organic polymeric compounds found therein, such as proteins, carbohydrates, and/or lipids. As will be appreciated by the skilled artisan, the bacteria selected are those capable of degrading these compounds to form intermediate metabolites, such as amino acids, sugars, and long chain fatty acids. Preferably, the bacteria within the first chamber 18 will also further degrade or ferment the intermediate metabolite products of hydrolysis. That is, fermentation, also referred to as "acidogenesis," is also believed to take place in the first chamber 18. Among other products, acidogenesis produces short chain acids, alcohols, such as butanol and ethanol, which are soluble in the digester stream, and gaseous products such as hydrogen and carbon dioxide. As used herein the term "hydrolysis" refers generally to the degradation of complex organic polymers to the smaller acidogenesis organic reaction products to form a digester stream containing these hydrolysis products.

Any of the hydrolysis or acid producing digestion systems known in the art can be used. A review of the microbiology of digestion is set forth, for example, in P. N. Hobson, et al., *Methane Production from Agricultural and Domestic Wastes,* Applied Science Publishers (1981). Exemplary hydrolysis and acid forming bacteria include species from genera including *Bacilli, Enterobacteria, Clostridia, Bacteroides,* and the like. Mixed and undefined bacteria cultures may also be used. Advantageously, bacteria do not have to be provided to the first chamber 18. That is, in a preferred embodiment of the invention, hydrolysis is achieved using indigenous microflora already present in the carbonaceous material. A pH level is maintained in the first chamber 18 so as to provide the desired hydrolysis conditions therein. Typically, the pH is from about 6.5 to about 8.5, and preferably about 7.5 to about 8.0.

After hydrolysis, the resultant digester stream is directed to a second chamber 20. Here the digester stream is subjected to a first methanation phase at thermophilic conditions (i.e., thermophilic methanation) to produce a gaseous product comprising methane from the digester stream treated in the first chamber 18. Preferably the thermophilic methanation phase is conducted at a temperature of between about 45° C. to about 60° C. Because the carbonaceous material in the first chamber 18 is heated as described above, advantageously no additional heat input is required in the second chamber 20 to maintain a temperature sufficient for thermophilic methanation, although heat can be added as desired. To maintain a desired temperature within the second chamber 20, insulation layer 22 is advantageously provided about the entire periphery of the digester 10. In addition, the second chamber 20 may also include a heater for maintaining the digester stream at a temperature sufficient for thermophilic methanation.

The digester stream may pass into the second chamber 20 continuously or intermittently, and is maintained in the second chamber 20 for a period of time sufficient to achieve the desired methane gas production. Typically, the digester stream is maintained in the second chamber 20 for about 2 to about 10 days, preferably for about 4 days.

In the second chamber 20, a biogas is produced by the action of the bacteria. The term "biogas" is known in the art, and is used herein to refer to the gaseous methanation product which includes methane gas, as well as carbon dioxide and other gases. Any of the methane producing thermophilic anaerobic digestion systems including bacteria capable of converting the hydrolysis products to methane gas, and other methane producing organisms known in the art can be used. Exemplary methane producing bacteria include species from genera including *Methanobacterium, Methanobrevibacterium, Methanospirillium,* and the like. As described above, in a preferred embodiment of the invention, methanation is achieved using indigenous microflora present in the organic carbonaceous material. The pH conditions within the second chamber 20 can be adjusted to provide the desired degree and rate of methane production. Typically, the pH is from about 6.5 to about 8.5, and preferably about 7.5 to about 8.0.

As will be appreciated by the skilled artisan, the high temperatures used in the thermophilic methanation phase of the invention create a high rate of reaction within the digester stream. This is advantageous in many respects. This can provide rapid degradation of the digester stream into biogas products, and thus shorten the retention time of the digester stream within thermophilic methanation chamber 20. Because of the high rate of reaction, the rate of biogas production is increased. This results in increased productivity and efficiency of the process.

Further, during thermophilic methanation, the biogas will rise to the top of the digester stream mixture (i.e., "bubble out" of the mixture) at a fast rate. This can be advantageous in providing a "self mixing" mechanism of the digester stream so that additional stirring or mixing mechanisms are not required to maintain a substantially homogenous mixture of digester stream and bacteria. In addition, the use of high temperatures in the thermophilic methanation stage can kill pathogens present in the carbonaceous material.

The biogas is collected from the second chamber 20 via line 24 and routed to a conventional gas storage tank (not illustrated). Alternatively, the biogas can be routed for other uses, such as the generation power for electricity, heating, drying, etc.

The effluent from the second chamber 20 is fluidly communicated to a third chamber 26. Here the digester stream is subjected to a second methanation phase at mesophilic conditions (mesophilic methanation). Additional gaseous product comprising methane is produced in the third chamber 26 from the continued degradation of the hydrolysis products produced in the first chamber 18. The mesophilic methanation phase provides several benefits, such as increased fermentation time, and a more complete reaction of the digester stream and thus increased methane gas production. Retention time within the third chamber 26 can be from about 2 to about 10 days, and is preferably about 5 days. The mesophilic methanation phase is conducted at a temperature of about 25° C. to about 35° C. No additional heat input is required in the third chamber 26.

In the third chamber 26, additional biogas is produced by the action of bacteria, preferably indigenous microflora present in the carbonaceous material. However, any of the methane producing mesophilic anaerobic digestion systems including methane producing bacteria and other methane producing organisms known in the art can be used. Exemplary methane forming bacteria are described above. As noted above, pH conditions can be adjusted within the third chamber 26 to provide the desired degree and rate of methane production, and pH can be from about 6.5 to about 8.5, preferably about 7.5 to about 8.0.

The biogas is collected from the third chamber 26 via line 28 and routed to a conventional gas storage tank (not illustrated). Alternatively, as noted above, the biogas can be routed for use in the generation of power such as electricity, heating, drying, etc. As illustrated, line 24 and line 28 direct the recovered biogas to a common storage tank via line 30, although as the skilled artisan will appreciate, the biogas recovered from the second chamber 20 and the third chamber 26 can be separately recovered and stored or utilized. The remaining digester liquid (i.e., the effluent) is removed from digester 10 via port 16 for further processing, recovery, or recycling. For example, the digester liquid can be used in aquaculture, such as by being added to ponds as a nutrient source for fish. In addition, the sludge remaining in the digester can be dried to a solid residue or by-product and utilized as a feed supplement, fertilizer, and the like.

There are several addition features of the apparatus and process of the invention which assist in the efficient and rapid anaerobic digestion of carbonaceous material. For example, digester 10 preferably includes a plurality of alternating upwardly projecting baffles 32 and downwardly projecting baffles 34 at spaced apart locations along the interior of the digester. The baffles 32 and 34 assist in mixing the digester stream to provide a homogeneous mixture within the interior of digester 10, so that additional mechanical mixing or stirring devices are not required.

In addition, upwardly projecting baffles 32 assist in separating chambers 18, 20 and 26. Further baffle 32 as illustrated which separates the first chamber 18 and the second chamber 20, further acts as a retaining wall to retain any insoluble, inorganic and non-digestible particles in the carbonaceous material within the first chamber 18. These particles, which typically include minerals, sand, humus, and the like, sink to the bottom of the first chamber 18 and can be removed via solid matter outlet 36.

A bacterial growth support 40 for increasing the surface area available for the growth of bacteria in the thermophilic methanation phase of the invention is also provided within the second chamber 20. This is advantageous in enhancing and increasing methane production. Preferably the bacterial growth support 40, comprises a biofilm. The biofilm can be, for example, a frame 42 formed of plastic or metal, and which includes a plurality of strips 44 formed of a plastic material such as nylon. Any suitable biofilm known to those skilled in the art may be employed.

Further, the apparatus of the invention advantageously includes a heat exchanger 50 in the third chamber 26 (i.e., the mesophilic methanation phase). Heat exchanger 50 can be any suitable heat exchanger known to those skilled in the art. An exemplary heat exchanger comprises coiled metal tubing connected to a circulation pump which pumps cool water through the tubing.

As noted above, the thermophilic methanation phase treats the waste at high temperatures of about 45° to 60° C. This increases the efficiency of methane production by increasing the degradation rate of the process. However, the thermophilic methanation step can result in a high heat output, which is wasted unless used otherwise. The heat exchanger 50 in the third chamber 26 recovers heat from the digester stream, thereby increasing the energy efficiency of the process because heat can be recovered and routed back into the process. For example, in a preferred embodiment of the invention, heat is recovered from digester stream in the third chamber 26 via heat exchanger 50, and is then routed back to the first chamber 18. This can be accomplished by routing the water heated in the heat exchanger 50 of the third chamber 26 to the aqueous liquid source which is in fluid communication with the aqueous liquid inlet 19. The thusly heated aqueous liquid can be used to heat the carbonaceous material. In another embodiment, the heat from the water heated in the heat exchanger 50 of the third chamber 26 may be routed to the aqueous liquid inlet 19 and may be used to further heat the organic carbonaceous material to the desired temperature. In this manner, less heated aqueous liquid or steam will be required to raise the temperature of the organic carbonaceous material to the desired temperature, thus providing a more energy efficient digester.

That which is claimed is:

1. A process for the anaerobic digestion of organic carbonaceous material, comprising:
   (a) hydrolyzing the organic carbonaceous material to produce a digester stream comprising hydrolysis products;
   (b) subjecting the digester stream to a first methanation phase at thermophilic conditions to produce a gaseous product comprising methane;
   (c) subjecting the digester stream to a second methanation phase at mesophilic conditions to produce further gaseous product comprising methane and concurrently recovering heat from said digester stream during said second methanation phase by directing an aqueous liquid source through a heat exchanger in said digester stream during said second methanation phase to thereby heat said aqueous liquid source; and
   (d) directing said recovered heat into step (a) of hydrolyzing to thereby heat the organic carbonaceous material by directing said heated aqueous liquid source from step (c) into fluid communication with said organic carbonaceous material of step (a).

2. The process of claim 1 wherein said hydrolyzing step further comprises heating the organic carbonaceous material.

3. The process of claim 2 wherein the step of heating said organic carbonaceous material comprises heating said material to a temperature of from about 45° C. to about 60° C.

4. The process of claim 2 wherein the organic carbonaceous material is heated by adding heated water thereto.

5. The process of claim 2 wherein the organic carbonaceous material is heated by adding steam thereto.

6. The process of claim 1 wherein said step (b) of subjecting the digester stream to a first methanation phase is carried out by contacting said digester stream to a plurality of films, said films supporting the growth of thermophilic bacteria, thereby increasing the surface area available for thermophilic treatment of said digester stream.

7. The process of claim 1 further comprising the step of recovering said gaseous product from each of said first methanation phase and said second methanation phase.

8. The process of claim 1 wherein said step (b) of subjecting the digester stream to a first methanation phase is carried out at a temperature of from about 45° C. to about 60° C.

9. The process of claim 1 wherein said step (c) of subjecting the digester stream to a second methanation phase is carried out at a temperature of from about 25° C. to about 35° C.

10. A substantially longitudinal apparatus for the anaerobic digestion of organic carbonaceous material, comprising in series:

(a) a first chamber having both a carbonaceous material inlet in fluid communication therewith and an aqueous liquid inlet in fluid communication therewith, said first chamber for containing carbonaceous material, aqueous liquid, and a source of bacteria, said bacteria being capable of digesting carbonaceous material to produce hydrolysis products;

(b) a second chamber in fluid communication with said first chamber for containing the digester stream, said second chamber having a source of anaerobic bacteria therein, said bacteria being capable of converting said hydrolysis products to methane gas; and (c) a third chamber in fluid communication with said second chamber for containing the digester stream, said third chamber having a source of anaerobic bacteria therein, said bacteria being capable of converting said hydrolysis products to methane gas, said third chamber further comprising a heat exchanger, means for directing an aqueous liquid source through said heat exchanger to thereby heat said aqueous liquid source and means for directing said heated aqueous liquid source from said third chamber to said first chamber to transfer heat from said third chamber to said first chamber concurrently with methane gas formation to thereby heat said organic carbonaceous material.

11. The apparatus according to claim 10, wherein said aqueous liquid inlet is also in fluid communication with an aqueous liquid source.

12. The apparatus according to claim 11, wherein said aqueous liquid source is equipped with a heater for heating the aqueous liquid.

13. The apparatus according to claim 10, wherein said first chamber is equipped with a steam inlet for heating the carbonaceous material and aqueous liquid.

14. The apparatus according to claim 10, wherein said bacteria of said first chamber are capable of hydrolyzing proteins, carbohydrates, and/or lipids within the carbonaceous material.

15. The apparatus according to claim 10, wherein said second chamber includes a bacterial growth support.

16. The apparatus according to claim 15, wherein said bacterial growth support comprises a biofilm including plastic material.

17. The apparatus according to claim 10, wherein said second chamber includes a heater for maintaining said digester stream at a temperature sufficient for thermophilic methanation.

18. The apparatus according to claim 10, wherein said second chamber includes a gas recovery line in fluid communication with an upper portion of said second chamber.

19. The apparatus according to claim 10, wherein said third chamber includes a gas recovery line in fluid communication with an upper portion of said third chamber.

20. The apparatus according to claim 18 or 19, wherein said gas recovery line is in fluid communication with a gas storage vessel.

21. The apparatus according to claim 18 or 19, wherein said gas recovery line is in fluid communication with a compressor.

22. The apparatus according to claim 10, wherein said first chamber includes a solid matter outlet at a lower portion of said first chamber.

23. The apparatus according to claim 10 wherein said apparatus further comprises a plurality of upwardly projecting baffles separating each of said reaction chambers from one another and having a predetermined height sufficient to define said reaction chambers while also allowing fluid communication between each of said reaction chambers.

24. The apparatus according to claim 10, wherein at least one of said first, second or third chambers includes one or more downwardly projecting baffles.

* * * * *